United States Patent
Shao et al.

(10) Patent No.: US 10,436,895 B2
(45) Date of Patent: Oct. 8, 2019

(54) PHASE CONFOCAL METHOD FOR NEAR-FIELD MICROWAVE IMAGING

(71) Applicant: ELLUMEN, INC., Arlington, VA (US)

(72) Inventors: Wenyi Shao, Laurel, MD (US); Todd R. McCollough, Barrington, IL (US); William J. McCollough, Earlysville, VA (US); Arezou Edalati, Arlington, VA (US)

(73) Assignee: ELLUMEN, INC., Arlington, VA (US)

( * ) Notice: Subject to any disclaimer, the term of this patent is extended or adjusted under 35 U.S.C. 154(b) by 327 days.

(21) Appl. No.: 15/342,368

(22) Filed: Nov. 3, 2016

(65) Prior Publication Data
US 2017/0356995 A1 Dec. 14, 2017

Related U.S. Application Data

(60) Provisional application No. 62/347,798, filed on Jun. 9, 2016.

(51) Int. Cl.
*G01S 13/89* (2006.01)
*G01N 22/00* (2006.01)
(Continued)

(52) U.S. Cl.
CPC .............. *G01S 13/89* (2013.01); *G01N 22/00* (2013.01); *G01S 13/887* (2013.01); *G01S 17/89* (2013.01);
(Continued)

(58) Field of Classification Search
CPC ...... G01S 13/89; G01S 13/90; G01S 13/0209; G01S 13/88; G01S 17/89; G01S 13/9035;
(Continued)

(56) References Cited

U.S. PATENT DOCUMENTS 3,806,929 A * 4/1974 Moore .................... G01S 13/64
324/76.12
5,233,541 A * 8/1993 Corwin .................. G01S 7/4802
342/195

(Continued)

FOREIGN PATENT DOCUMENTS

WO    WO-2006/028397 A1    3/2006

OTHER PUBLICATIONS

U.S. Appl. No. 15/094,368, filed Apr. 8, 2016, Ellumen, Inc.
(Continued)

*Primary Examiner* — Olumide Ajibade Akonai
(74) *Attorney, Agent, or Firm* — Foley & Lardner LLP

(57) ABSTRACT

An efficient RADAR imaging method that is able to detect an object within an interested area. This method uses electromagnetic waves transmitted by one or many transmitters to illuminate the interested area, and then estimates the phase shift of the scattered wave of an object according to the path that the electromagnetic wave propagated. By reversing the phase of the obtained scattered signal to the transmitters' position, an image is constructed for the entire interested area according to the correlation of signals in all channels. The present method works in the frequency domain. It produces a microwave image by using the phase and magnitude of the obtained signal, or using the phase information only. Other unique features include the way it synthesizes the signals obtained in multiple channels and at multiple frequencies. Its overwhelming high efficiency makes rapid microwave imaging and real-time imaging possible.

18 Claims, 11 Drawing Sheets

(51) Int. Cl.
*G01S 17/89* (2006.01)
*G01S 13/88* (2006.01)
*A61B 5/05* (2006.01)
*G01S 15/89* (2006.01)

(52) U.S. Cl.
CPC ..... *A61B 5/0507* (2013.01); *A61B 2562/0228* (2013.01); *G01S 15/89* (2013.01)

(58) Field of Classification Search
CPC .......... G01S 7/411; G01S 13/867; G01S 2013/9375; G01S 2007/2883; G01S 15/89; G01S 13/887; G01S 13/9023; G01S 7/41; A61B 5/0507; A61B 2562/0228; A61B 5/4312; G06T 2207/10044; G06K 9/0063; G06K 9/00805; G06K 2209/21; G06F 17/14
See application file for complete search history.

(56) References Cited

U.S. PATENT DOCUMENTS

| | | | |
|---|---|---|---|
| 6,061,589 A | 5/2000 | Bridges et al. | |
| 6,389,084 B1* | 5/2002 | Rupp | H04L 25/03012 342/101 |
| 6,972,714 B1* | 12/2005 | Baharav | G01N 22/00 342/175 |
| 2006/0147090 A1* | 7/2006 | Yang | H04N 5/145 382/107 |
| 2006/0214836 A1* | 9/2006 | Baharav | G01S 13/89 342/22 |
| 2007/0257188 A1* | 11/2007 | Robertson | G01J 5/522 250/252.1 |
| 2008/0079625 A1* | 4/2008 | Weems | G01S 7/20 342/22 |
| 2008/0100510 A1* | 5/2008 | Bonthron | G01S 7/024 342/373 |
| 2012/0084036 A1* | 4/2012 | Booman | G01R 1/06766 702/79 |
| 2013/0002488 A1* | 1/2013 | Wang | G01S 13/34 342/377 |
| 2013/0106651 A1* | 5/2013 | Goldstein | G01S 13/9035 342/25 F |
| 2016/0139259 A1* | 5/2016 | Rappaport | G01S 7/003 342/21 |
| 2017/0131399 A1* | 5/2017 | Ioannidis | G01S 13/89 |

OTHER PUBLICATIONS

Elise C. Fear et al., Enhancing Breast Tumor Detection with Near-Field Imaging, IEEE Microwave Magazine, Mar. 2002, pp. 48-56.
Elise Fear et al., Microwaves for Breast Cancer Detection?, IEEE Potentials, 2003, pp. 12-18.
Hooi Been Lim et al., Confocal Microwave Imaging for Breast Cancer Detection: Delay-Multiply- and Sum Image Reconstruction Algorithm, IEEE Transactions on Biomedical Engineering, vol. 55, No. 6, Jun. 2008, pp. 1697-1704.
Jason Langley et al., A Model-Based 3D Phase Unwrapping Algorithm Using Gegenbauer Polynomials, Physics in Medicine and Biology, 54, 2009, pp. 5237-5252, IOP Publishing.
Jason Langley et al., Unwrapping Magnetic Resonance Phase Maps With Chebyshev Polynomials, Magnetic Resonance Imaging, 27, 2009, pp. 1293-1301.
Lei Guo et al., Optimization-Based Confocal Microwave Imaging in Medical Applications, IEEE Transactions on Antennas and Propagation, vol. 63, No. 8, Aug. 2015, pp. 3531-3539.
Xu Li et al., A Confocal Microwave Imaging Algorithm for Breast Cancer Detection, IEEE Microwave and Wireless Components Letters, vol. 11, No. 3, Mar. 2001, pp. 130-132.
Yao Xie et al., Multistatic Adaptive Microwave Imaging for Early Breast Cancer Detection, IEEE Transactions on Biomedical Engineering, Aug. 2006, pp. 1647-1657, vol. 53, No. 8.

* cited by examiner

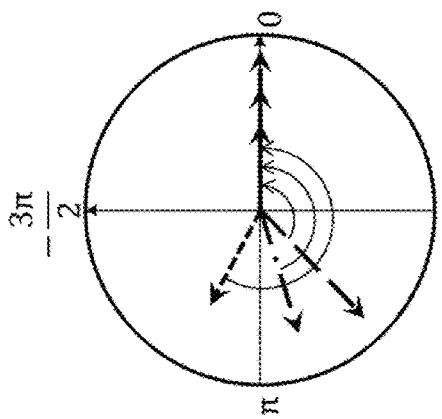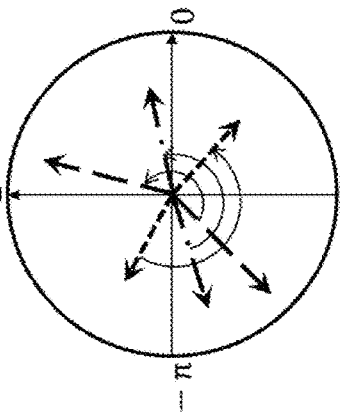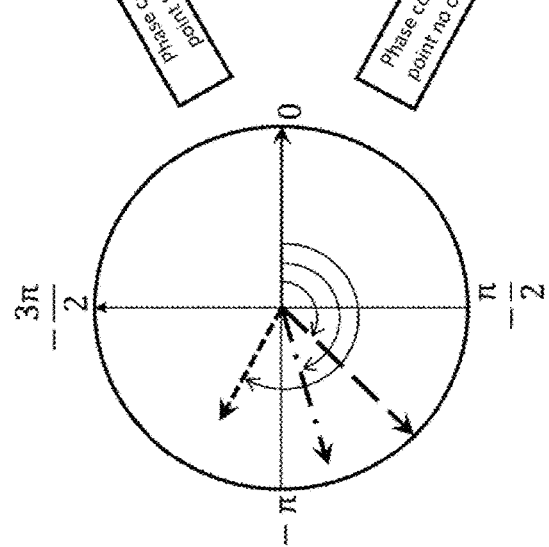
Figure 7

PHASE CONFOCAL METHOD FOR NEAR-FIELD MICROWAVE IMAGING

This application claims priority to U.S. Provisional Application No. 62/347,798, filed Jun. 9, 2016, whose entire contents are incorporated herein by reference.

BACKGROUND OF THE INVENTION

The present disclosure pertains generally to near-field microwave imaging.

In the art of microwave detection, near-field microwave imaging attempts to detect the profile of an object less than one wavelength to several wavelengths away from the antennas by measuring an electromagnetic scattered field. Typically, many antennas are placed near the object and antennas take turns transmitting a waveform that illuminates the object, while the other antennas serve as receivers. Alternatively, the detection can use a small number of movable antennas to observe the object in multiple locations. After detection, an algorithm is applied to process the collected data to form an image displaying the object's profile. Typical applications are buried-object detection, nondestructive surveys, and biomedical examinations.

There are two main approaches to active microwave imaging: microwave tomography and RADAR-based imaging. Microwave tomography involves reconstructing an image in terms of a quantitative description of any objects present such as a dielectric constant or conductivity, impedance, or local velocity. This approach usually is ill posed and is performed by iteratively comparing measurement data with numerical simulation data, which can be a slow and time consuming process. In contrast to microwave tomography, RADAR-based imaging methods reconstruct an image in terms of a qualitative description of any objects present and instead aim to find the profile of an object. More specifically, the purpose of a RADAR-based method is to distinguish the object's size, shape, and location instead of showing a distribution of a physical parameter in the entire area.

FIG. 3A, FIG. 3B, and FIG. 6 can help describe how a conventional RADAR based method works, in which the time arrival information and amplitude of scattered signals are utilized to identify the presence and location of a significant scatter. The conventional algorithm involves calculating the flight time of the signal travelling in space or a medium then back-propagating the signal to the transmitters' position with corresponding time-delay compensation. In this approach, a time domain UWB (ultra-wide band) signal is often used to illuminate an object and the scattered signal is measured from numerous places (in this case from three different places). The Euclidean distance from each receiver to the source through a focal point (a position in the area under exploration) is estimated and each signal is compensated for its time delay or shift. A flight time from positions in the interested area to antennas (or probes in simulation) is individually calculated. In locations with no objects present, the shifted signals are less correlated and will result in less amplitude when they are summed, as shown in FIG. 3A. In the object's location, the shifted signals are highly correlated in time and result in greater amplitude when summed, as shown in FIG. 3B. As a result, a qualitative image of the object under investigation is obtained. This kind of approach is expected to achieve a high-resolution imaging effect since it uses a UWB signal containing many frequency components.

A discussion of time domain confocal imaging algorithms is disclosed in "A Confocal Microwave Imaging Algorithm for Breast Cancer Detection" by Xu Li et al. in IEEE Microwave and Wireless Components Letters, Vol. 11, No. 3, March 2001 and "Enhancing Breast Tumor Detection with Near-Field Imaging" by Elise C. Fear et al. in IEEE Microwave Magazine, March 2002. The entire contents of these publications are incorporated herein by reference for such techniques as well as systems, methods and other techniques related to microwave imaging.

SUMMARY OF THE INVENTION

The present inventive concepts, titled phase confocal method (PCM), belong to a RADAR-based imaging approach. Unlike previous RADAR-based approaches which operate in the time domain, the present method processes signals in the frequency domain. While the conventional RADAR-based approaches calculate the time delay of a signal in the time-space domain, the present inventive concepts calculate a phase delay (or a phase shift) in the frequency-space domain. There is often a demand to detect objects existing in a dispersive medium in which the wave propagation speed varies with frequency. For example, in biomedical microwave detection, human-body tissue is dispersive at microwave frequencies and in ground-penetration detection, soil is a dispersive medium. In these scenarios, components of different frequencies in the UWB signal spectrum will take different paths across the air-medium interface and propagate at different speeds in the medium. The conventional RADAR-based approaches calculate the UWB signal flight time between the sensor and the object, which requires that the distance and speed are correctly estimated. However, the conventional approaches assume that many frequency components in the UWB signal travel together—they take the same path and travel with the same speed. This approximation leads to an inaccurate flight time estimation, and finally degrades the image quality. In the present method, phase delay instead of time delay is calculated and utilized to shift the phase of the acquired signal at each frequency. By treating each frequency individually an accurate delay (or shift) is found and utilized. Therefore, the present method is able to fully take advantage of the UWB spectrum.

The present inventive concepts allow using the phase information alone, or alternatively a combination with amplitude information to reconstruct an image. When using the phase information only, all the phase signals are assumed as unit vectors whose magnitude is unity. As the phase delay of all signals are correctly compensated (shifted), in the locations an object is present, the shifted phase signals will have a very small difference. In those positions where no object is present, there will be large differences between these shifted phase signals. Next, two methods are proposed to calculate the pixel values to form an image. In the first, when both phase information and amplitude information are used, the phase-shifted signals are summed following the principle of vector addition. In the second method, the 2-D distance from the unit vectors to their average value is implemented to compute the pixel value of an image. The data processing is in the frequency domain and the signals are treated as complex numbers, which is different from a conventional algorithm that processes real numbered data in the time domain. PCM can reconstruct an image using a single frequency signal and also multiple frequency signals. PCM also has the advantage of being able to accurately estimate the contribution of multiple frequency components.

Although the present method processes data in the frequency domain, experiments can be performed in the time domain and converted to the frequency domain by a Fourier transform.

BRIEF DESCRIPTION OF THE DRAWINGS

Embodiments will now be described in more detail with reference to the accompanying drawings, given only by way of example, in which:

FIG. 7 shows the phase shift of the signal as it propagates for some particular distances in different channels from the same start position.

FIG. 7A shows a phase compensation step where the wave back-propagated from the reception end to the transmission end through an object's location such that after compensation phases are coherent.

FIG. 7B shows a phase compensation step where the wave back-propagated from the reception end to the transmission end through a focal point where no object is present such that after compensation phases are incoherent.

DETAILED DESCRIPTION OF EMBODIMENTS OF THE INVENTION

Figure 1:
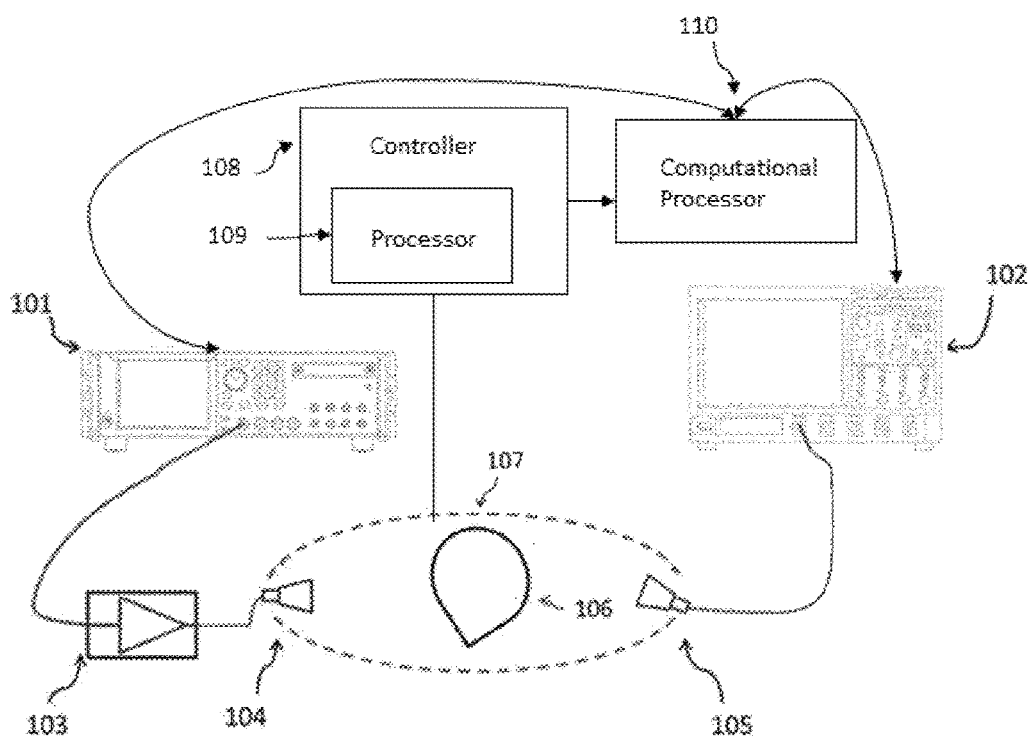
FIG. 1 shows the time-domain embodiment of the microwave near-field imaging system.

The measurement process can be carried out either in the time domain or in the frequency domain. When measurements are carried out in the time domain, a system as illustrated in FIG. 1 is typically used for electromagnetic signal collection. The transmitter 104 and the receiver 105 are usually UWB antennas which can individually move along a rail system 107 to send/receive a signal in many positions. A time-domain signal that has a wide-band characteristic is produced by a waveform generator 101. By amplifying the signal with a wide-band amplifier 103, the electromagnetic energy radiated by the transmitter antenna 104 is large enough for detection. The scattered signal of the object 106 is received by at least one receiver antenna 105 and then recorded on an oscilloscope 102. The object 106 may be in air, in a coupling medium, or within another object. By moving the transmitter 104 and the receiver 105 on the rail system 107, the object 106 is fully observed. A controller 108 is configured to move and rotate the transmitter 104 and the receiver 105 on the rail system 107. The controller 108 contains a processor 109 programmed with computer software to allow it to perform its control functions. An image showing the location and profile of object 106 can be achieved by processing the received data by means of a computational processor 110. The computational processor 110 has one or more processors and a memory programmed with computer software that performs the functions described herein. Alternatively, hardware may be used instead of or in addition to software. The computational processor 110 can further communicate with the waveform generator 101 and oscilloscope 102.

Figure 2:
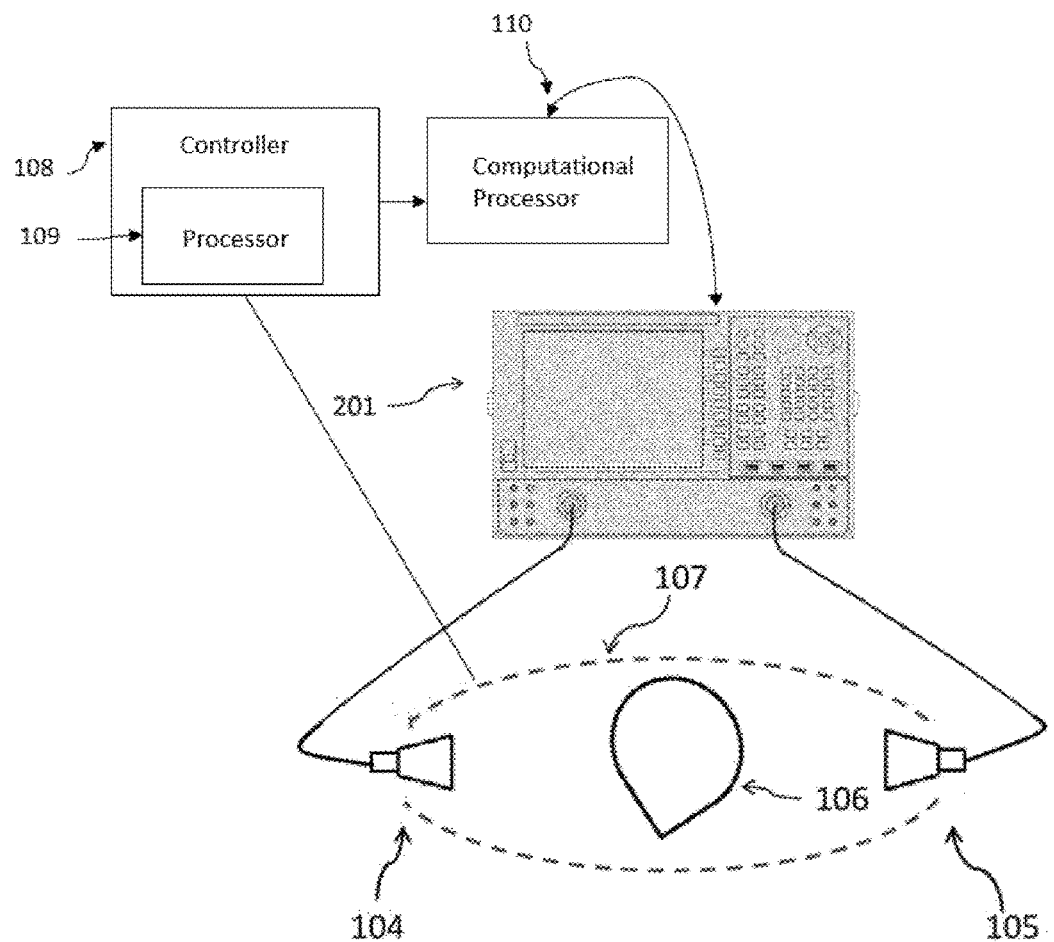
FIG. 2 shows the frequency-domain embodiment of the microwave near-field imaging system.
Figure 3A:
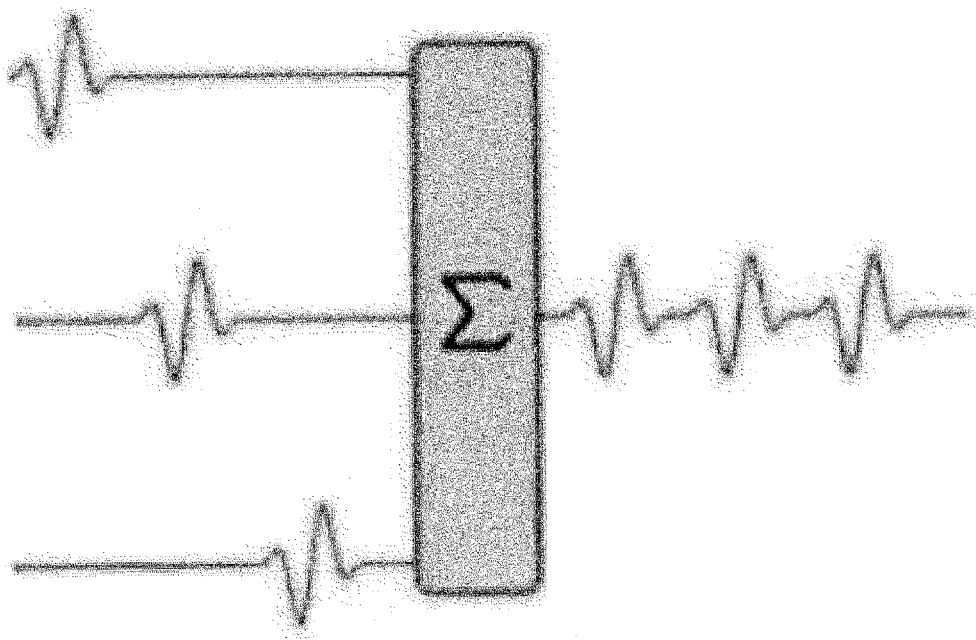
FIG. 3A shows signals less correlated in time result in a lower amplitude when they are summed.
Figure 3B:
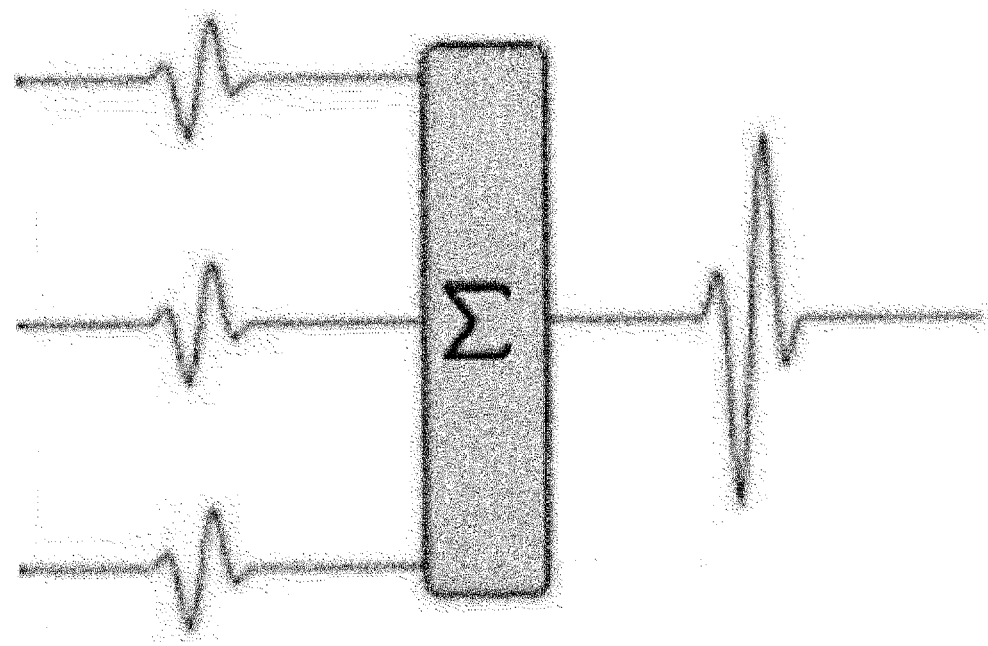
FIG. 3B shows signals highly correlated in time reinforce each other when they are summed.

When measurements are carried out in the frequency domain, a system as illustrated in FIG. 2 is typically used for electromagnetic signal collection. A vector network analyzer (VNA) 201 is typically implemented to send and receive signals. By clarifying the start frequency, end frequency, and a number of frequencies, the VNA uses a "frequency sweeping" mode to continually send out time domain sinusoid waves at assigned discrete frequencies in turn until waves at all frequencies are received. A controller 108 is configured to move and rotate the transmitter 104 and the receiver 105 on the rail system 107. The transmitter antenna 104 and receiver antenna 105 can be narrow band antennas for a single frequency or a narrow band survey or wide band antennas to catch discrete frequencies over a wide band. The controller 108 contains a processor 109 to allow it to perform its control functions. An image showing the location and profile of object 106 can be achieved by processing the received data by means of a computational processor 110. The computational processor 110 can further communicate with the vector network analyzer 201.

The antenna arrangement in FIG. 1 and FIG. 2 is able to achieve the same goal as using many antennas in fixed positions but has the advantage that moving the antennas allows for more possible positions to be covered. An advantage of using a single transmitter and receiver is that unwanted couplings between antennas when antennas are close can be prevented. However, in some embodiments of the present invention it is possible to use multiple fixed antennas where antennas take turns transmitting and the other antennas receive. In some embodiments it is possible to move/translate the object 106 and/or transmitter antenna 104 and receiver antenna 105 in the z direction. In these embodiments the movement and translation in the z direction is performed by the controller 108.

There are some advantages and disadvantages to collecting data in either the time domain or the frequency domain. An advantage of a time domain measurement over a frequency domain measurement is that a reconstruction algorithm based on time domain data employs the scattered field of the object over an entire wideband rather than a few selected discrete frequencies. As such, high resolution is better able to be achieved in the reconstructions. A downside of a time domain measurement over a frequency domain measurement is that time domain signals are often distorted in shape as they propagate in a dispersive and/or lossy medium. This may degrade the image quality in the reconstruction. An advantage of a frequency domain measurement is that the signal-to-noise ratio is usually better than that in the time domain.

Unlike other methods the present inventive concepts can use data recorded from a VNA directly. When the measurement is executed by the system in FIG. 2, the recorded signals on the VNA are usually in the form of S parameters ($S_{21}$). The present method is able to adopt the $S_{21}$ signal directly without a conversion to electrical-field data. In conventional microwave imaging techniques, this kind of conversion is usually challenging because it contains both simulation and experimental steps, and then new noise from this additional experiment will be brought into subsequent signal processing. The reason that the present method can use the phase of $S_{21}$ parameter is because it is equal to that of the electrical field. Meanwhile, the magnitude of $S_{21}$ can be directly substituted into the present method, without a need to know the ratio to the magnitude of electric field (in conventional imaging approaches the S parameters must be converted to electric field). When measuring with the VNA, the transmitted waves and received waves are converted to the frequency domain and a division calculation is carried out in the VNA to obtain the transmission coefficients ($S_{21}$ and $S_{12}$), which is often applied in the analysis of a two-port network. The transmission coefficient or S parameters can be viewed as the signal of a frequency domain response system and be used in the image reconstruction process. The S parameters are complex numbers and have magnitude and phase. The phase of $S_{21}$ represents the phase difference between the output signal and the input signal. When S parameters are measured by a vector network analyzer their phase is shown from 0 to 360°. This does not mean the phase change in the system must be less than 360°. For example, if the distance a wave traveled from a transmitter to a receiver is 1.5 wavelengths the phase actually changes 1.5*2π (540°) during the propagation. On the reception side, the phase of $S_{21}$ observed is 180°.

A discussion of S parameters is contained in "Microwave Engineering", $3^{rd}$ edition, by David M. Pozar, which is incorporated by reference in its entirety for the discussion of such parameters.

Figure 4:
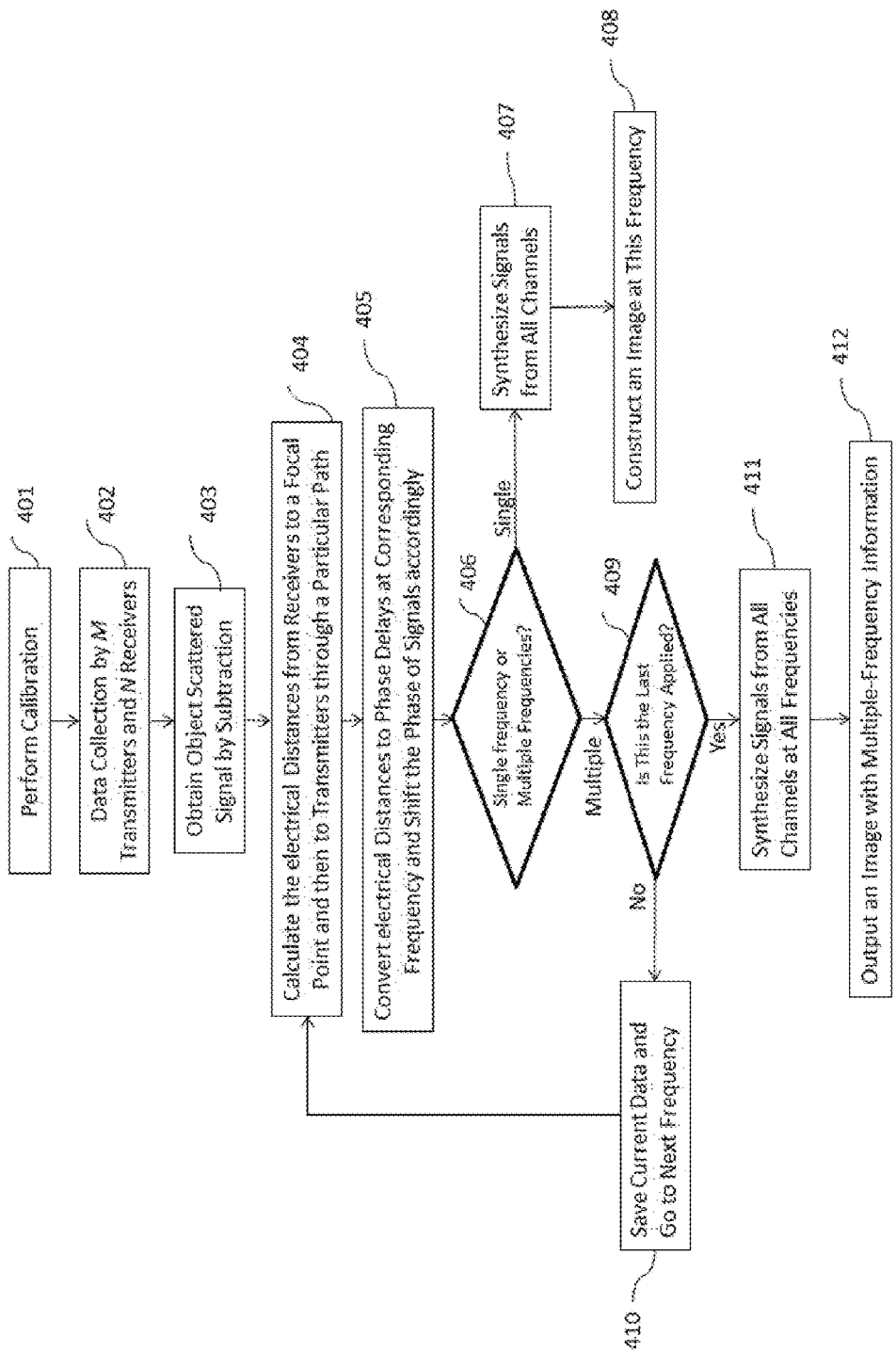
FIG. 4 is a flow chart showing exemplary steps for the present imaging method.

FIG. 4 shows a flow chart of exemplary procedures for the present imaging method.

The first step 401 is to perform any calibration necessary prior to data collection. The second step 402 is to collect the electromagnetic signal using the system of FIG. 1 or 2. There are usually two steps in the measurement. The first step is to measure the incident field, in which no object presents in the middle of the antenna ring 107. The second step is to measure the total field—as the object presents in the middle area of the antenna ring 107—with the same antenna arrangement. In both steps, the transmitter stops at the same M locations. At each stop, at least one receiver is utilized to collect signals at the same N locations. Hence, there are two M×N series of signals acquired in the entire experiment. The time-domain data obtained from a time domain measurement can be converted to frequency-domain data by a Fourier transform. Regardless of whether the measurement is carried out in the time domain or frequency domain, the acquired incident field signal and total field signal contains the effect of antennas (time delay or phase delays when the signal goes through the antennas) which has to be calibrated out before data can be used for imaging.

Figure 5:
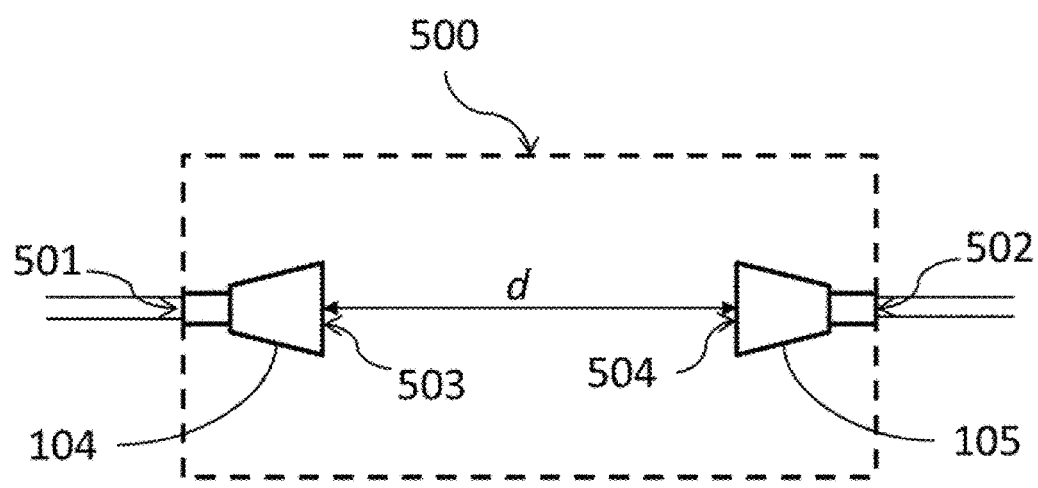
FIG. 5 shows a 2-port network to simplify a transmission-reception system.

FIG. 5 shows a simplified two-port system 500 to represent a measurement system. In RADAR based methods, there is a need to obtain the time shifts or phase shifts (in present method) of the signal between the antenna ends 503 and 504 when the antennas are in any pre-selected places. The effects due to the cables connected to antennas are taken to already be calibrated out by a standard VNA calibration for a frequency-domain measurement or by a simple estimation of the time delay in the cable for a time-domain measurement. FIG. 5 herein focuses on the calibration of the antennas' effect only. The input of 500 is the signal delivered to the port of a transmitter antenna 104 and the output is the signal obtained at the port of the receiver antenna 105. Two antennas are face-to-face placed for a known distance d. The wave flight time between two antennas is calculated as $$\frac{d}{v},$$

where v is the wave speed travelling in air. The phase delay between two antennas is $$\frac{d}{\lambda} \cdot 2\pi,$$

where λ is the wavelength. Assuming the same antennas are utilized for 104 and 105, by a simple transmission-reception test, the time delay in one antenna (from the antenna's port 501 to the antenna's end 503, or 504 to 502) can be calculated as $$\frac{T-t}{2},$$

where T denotes the time shift between the measured output signal and input signal, and $$t = \frac{d}{v}.$$

A similar method can be used to calculate the phase delays in the antenna which can be written as $$\frac{\Phi - \varphi}{2},$$

where Φ denotes the phase difference between the output signal and input signal, and $$\varphi = \frac{d}{\lambda} \cdot 2\pi.$$

With this approach accurate time shifts of waves propagating in a medium (from antenna end 503 to antenna end 504) in real detections can be obtained by T'−(T−t), or phase shifts by Φ'−(Φ−φ), where T' and Φ' is the measured shift in real detections from 501 to 502. In some embodiments the calibration step 401 can be performed after the data collection step 402.

Step 403 involves obtaining scattered signals by a subtraction process. The path that a signal travels from one of the M locations to one of the N reception locations is called a channel. In each channel, by subtracting the incident field from the total field, the scattered field of the object is obtained and saved in an M×N matrix, representing the measured results for corresponding transmission locations and reception locations.

Figure 6:
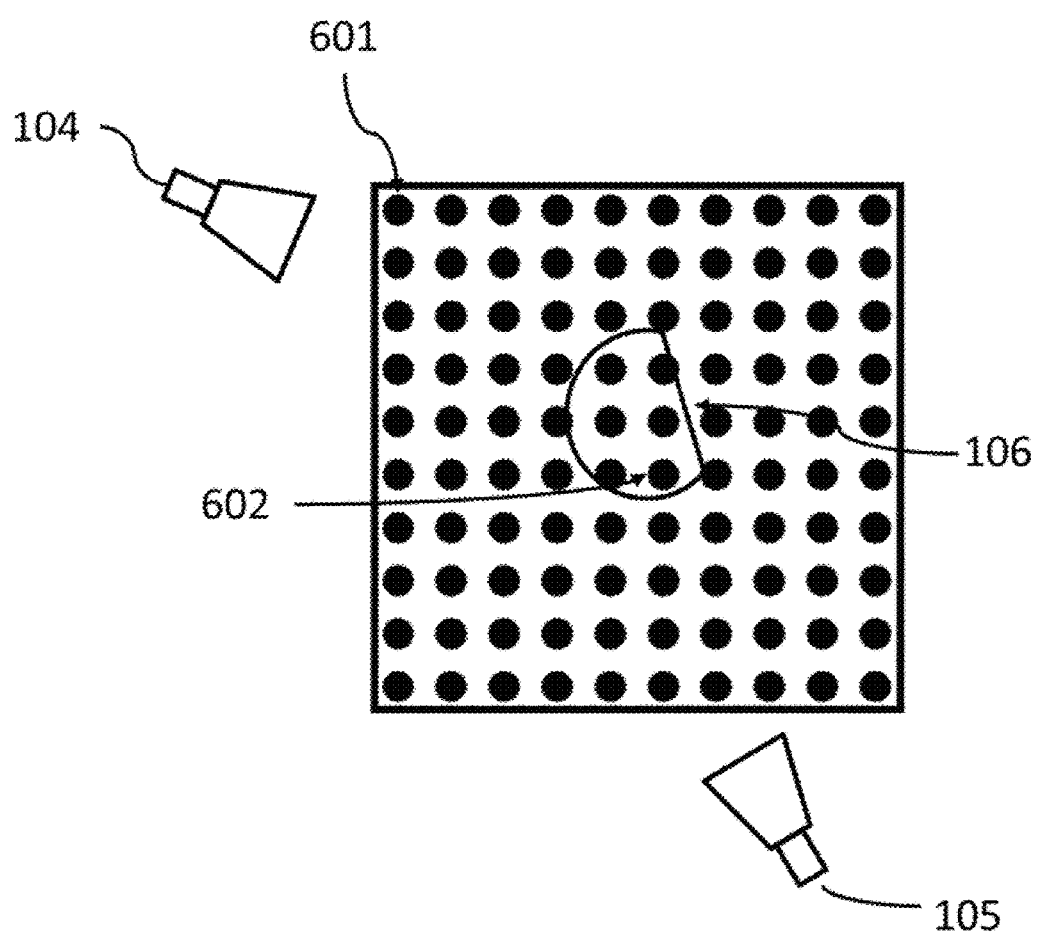
FIG. 6 shows the interested area to be imaged which is composed of many focal points.

In step 404 the electrical distances from receivers to focal points and then to transmitters is calculated. This distance can in some cases include the physical distance from receivers to focal points and then from the focal points to transmitters which can be calculated by using the Euclidean distance formula and knowing the Cartesian coordinates. The electrical distance calculation can be elaborated with the help of FIG. 6. In FIG. 6, the interested area to be imaged is meshed into many grids. Each grid is imagined as a focal point (each dot). For each focal point, it is imagined that the wave propagates from a transmitter 104 to the current focal point, and scatters at each position and then the scattered wave is acquired by a receiver 105. To clarify, physical scanning of each different focal point is not performed. The algorithm described above is used to computationally focus on each position (focal point), using the signals from a single set of measurements. This process is regarded as a beamforming method. The distance the wave propagates in this path is computed. The distance calculation is repeated for all focal points in the entire area, including those the object 106 possesses or does not possess (this is actually unknown before an image is obtained). Note that when the object is enclosed in a medium other than air, refraction which occurs on the air-medium interface must be taken into account. Therefore, the traveled distance d is a combination of electrical distances in different media and has taken refractions into account.

In step 405, the phase change of the wave as it propagates is calculated by using the equation $$\frac{d}{\lambda} \cdot 2\pi$$

at a particular frequency. FIG. 7, FIG. 7A, and FIG. 7B illustrates the detail of step 405. FIG. 7 shows the phase of a wave shifts clockwise when the wave has a zero initial phase at a transmitter, which propagates in three different paths, by a different distance, and arrives at three different receivers. The magnitude attenuates with the distance it traveled. It is necessary to compensate the phase of the obtained signals at the receivers by $$\frac{d}{\lambda} \cdot 2\pi$$

for each channel. The phase of the obtained signals will rotate back by $$\frac{d}{\lambda} \cdot 2\pi$$

counterclockwise, as if all the signals back-propagate to their initial position. As a result, when the computation focuses on a focal point like 602 where the object is present and the wave really scattered at this focal point, the phase of all the signals will return to their common initial phase after phase compensation (the phases are coherent), as shown in FIG. 7A. On the other hand, at focal points like 601 where no object is present, the phases are incoherent after phase compensation as shown in FIG. 7B because the waves did not scatter due to hitting an object in these positions.

In the m-n channel, where the phase of the signal collected by the $n^{th}$ receiver is $\psi_{mn}$, the phase after compensation (back-propagating to the transmitter's place) $\psi'_{mn}$ is $$\psi'_{mn} = \psi_{mn} + \Delta\psi_{mn}$$

$\Delta\psi_{mn}$ is the phase delay in air, that is, the phase delay to the focal point based on distance.

In step 406 a decision is made if there is single frequency or multiple frequency data that has been collected. If single frequency data is collected then the signals are synthesized in step 407. If multiple frequency data is collected, then a check is made to determine if this is the last frequency applied in step 409. The last frequency is the highest frequency present in a set of multiple frequencies. If the last frequency is not yet reached, then in step 410 the current data is saved and the next frequency is selected. Then step 404 is started with the next frequency. If the last frequency is applied, then the signals at all frequencies are synthesized in step 411.

If the detection uses a single frequency (step 407), a total of M×N signals (M×N complex numbers) will be synthesized to calculate the pixel value at each focal point, and an image showing the entire distribution can be produced.

Figure 8:
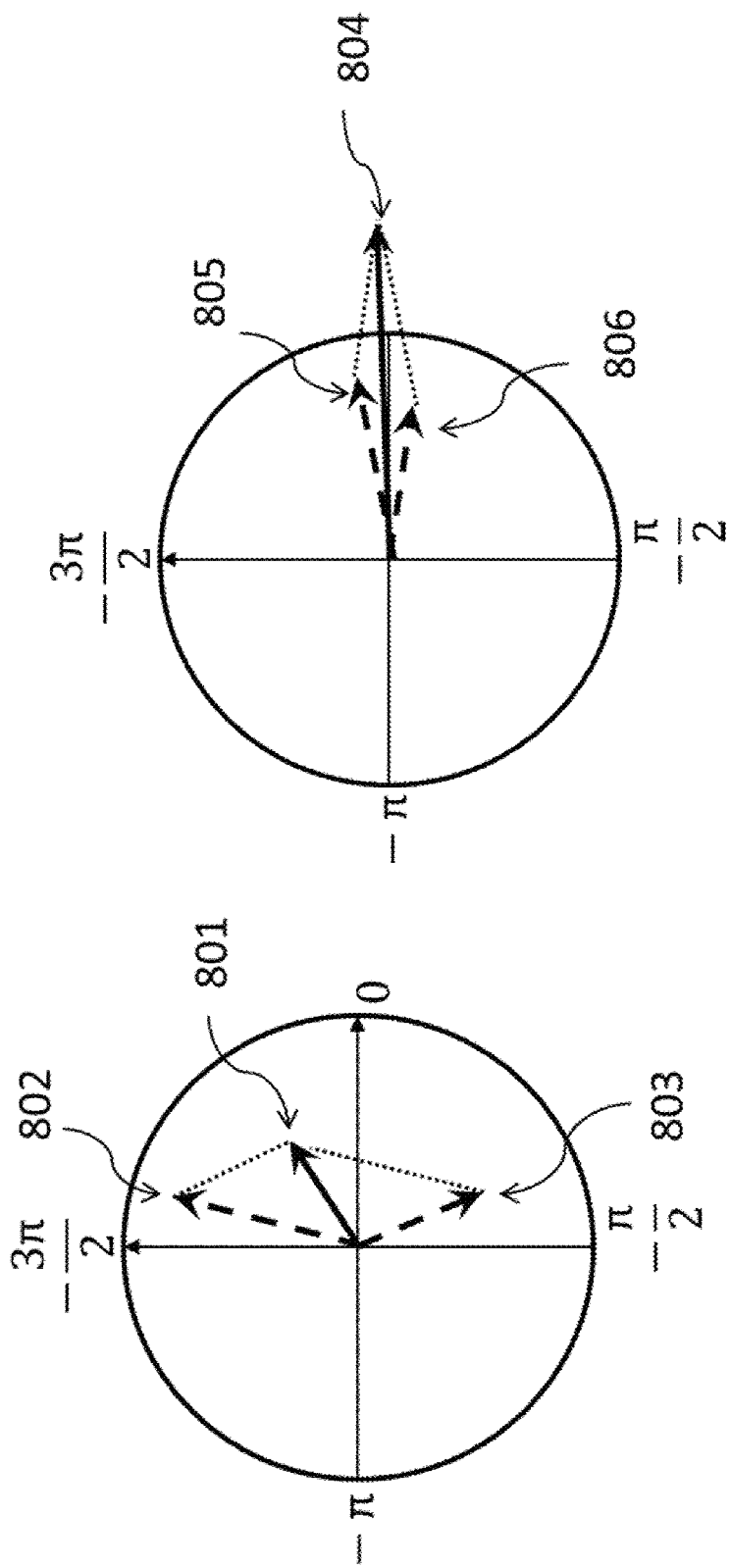
FIG. 8A shows the sum of two vectors having a big phase difference results in a small magnitude vector.
FIG. 8B shows the sum of two vectors having a small phase difference results in a big magnitude vector.

Theoretically, the compensated phase values LP' are expected to be identical in all channels, if the same detection signal was used by the transmitters. In the present invention, two separate methods are developed to synthesize signals. In both methods, the complex-number signals are treated as vectors. The first method to synthesize signals is vector addition. In FIG. 8A and FIG. 8B (which show two signals as a simplification), two vectors are shown in dashed line arrows as two obtained signals after the phase compensation step. FIG. 8A shows an occasion where two signals 802 and 803 have a large difference in phase after the phase compensation step. Their sum, shown in a solid line vector 801 having a short length, is of a small magnitude, which indicates the object is less likely residing in the current focal point. On the other hand, FIG. 8B illustrates an occasion where two signals 805 and 806 have a relatively small difference in phase, which results in a large magnitude in the summation vector 804, indicating the object is more likely to be residing in the current focal point. Signals 805 and 806 are signals from different channels (different receivers) looking at the same focal point. The magnitude of the result will be converted linearly to a pixel value in the final image (Step 408 or 412). It is optional to compensate the magnitude of signals due to spread out and loss in the medium before the sum.

Figure 9:
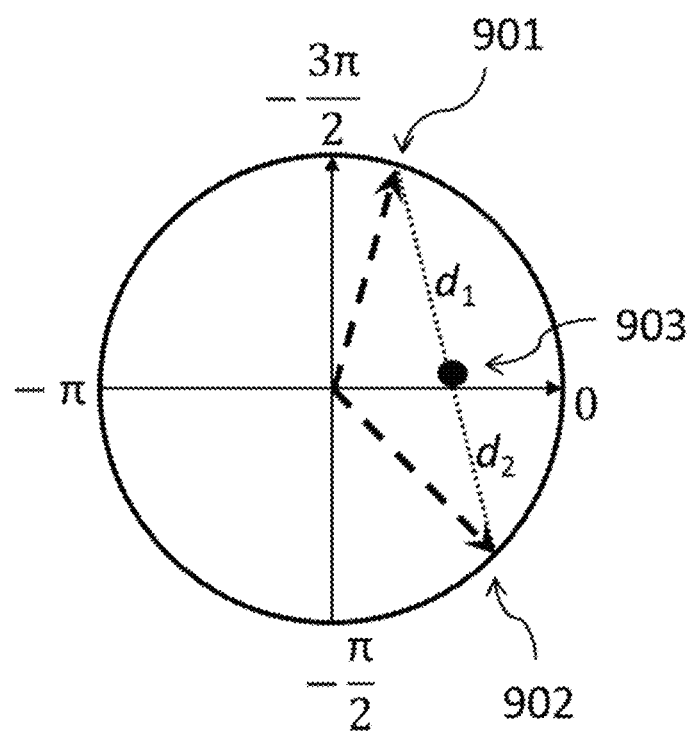
FIG. 9 shows the distances from two vectors to their mean position.

The second method to synthesize the M×N signals is relatively complex, but is more likely to achieve a better performance. In this method, the magnitude of the complex-number signals is completely ignored such that all of the signals are thought of as unit vectors only. Then, instead of an addition computation, the average of the squared distance from all unit vectors to their mean position is computed. As an example, FIG. 9 shows a case where two signals 901 and 902 are involved in the calculation. A round dot 903 represents the mean position (or middle point) of the two signals. The average of the squared distance from the two unit vectors to their mean position is calculated as $\frac{1}{2}(d_1^2+d_2^2)$, where $d_1$ and $d_2$ are the distances from the unit vector 901 and 902 to their mean position respectively. Further, as there are M×N signals involved in the computation, the equation used is $$\frac{1}{M \times N} \sum_{m=1,n=1}^{M \times N} d_{m,n}^2$$

The variable $d_{m,n}$ is the average of the squared distance from all unit vectors to their mean position for each of the M×N signals. The mean position of M×N signals $$\left(\frac{x_1+x_2+\ldots x_{M\times N}}{M\times N}, \frac{y_1+y_2+\ldots y_{M\times N}}{M\times N}\right)$$

in the Cartesian coordinates can be written in another form:

$$\left(\frac{1}{M\times N}\sum_{m=1,n=1}^{M\times N}\cos(\psi_{m,n}), \frac{1}{M\times N}\sum_{m=1,n=1}^{M\times N}\sin(\psi_{m,n})\right),$$

where $\psi_{m,n}$ is the phase of the M×N signals. A simpler statistic form can be used to show what is calculated:

$$Q(\vec{r})=\sigma^2(\cos(\psi'_{m,n}))+\sigma^2(\sin(\psi'_{m,n}))$$

where $\sigma^2$ represents a variance computation. As a result, in locations where an object is present, a small variance value is present and can be converted to a large pixel value in the image by a reciprocal computation:

$$P(\vec{r}) = \frac{1}{Q(\vec{r})}$$

$P(\vec{r})$ will be the pixel value of the image in the position $\vec{r}$.

The PCM uses the phase of S (when measuring with a VNA) which actually represents the phase change from the port of transmitter 104 to the port of receiver 105, if the VNA is calibrated correctly in advance. More specifically, the phase change consists of five parts: phase change in the connector on the transmitter end ($\Phi_{TC}$), phase change in the transmitter antenna ($\Phi_T$), phase change of propagation in space ($\Delta\psi_{space}$), phase change in the receiver antenna ($\Phi_R$), and phase change in the connector on the receiver end ($\Phi_{RC}$). The total phase change is represented in the following equation:

$$\Delta\Phi=\Phi_{TC}+\Phi_T+\Delta\psi_{space}+\Phi_{RC}+\Phi_R$$

In single frequency detection, since $\Phi_{TC}$, $\Phi_T$, $\Phi_{RC}$, $\Phi_R$ are fixed in all channels, there is only a need to compensate the phase change in space, i.e., $\Delta\psi_{space}$. There is no need to know the other four terms, nor are they used in the single-frequency PCM.

When multiple frequencies or a UWB signal is applied, the phase delay for each frequency component will take turns being calculated and compensated. The phase delay in the connectors and antennas ($\Phi_{TC}+\Phi_T$,$\Phi_{RC}+\Phi_R$) varies with frequency, so these four terms have to be taken into account in the phase compensation when applying multiple-frequency PCM. As a result, $\Delta\Phi$ containing five parts will all be applied in the phase compensation step in multiple-frequency PCM instead of only using $\Delta\psi_{space}$ as in single-frequency PCM. The value of $\Phi_{TC}+\Phi_T$ and $\Phi_{RC}+\Phi_R$ can be found by a simple test on the VNA in advance of the data collection.

Figure 10:
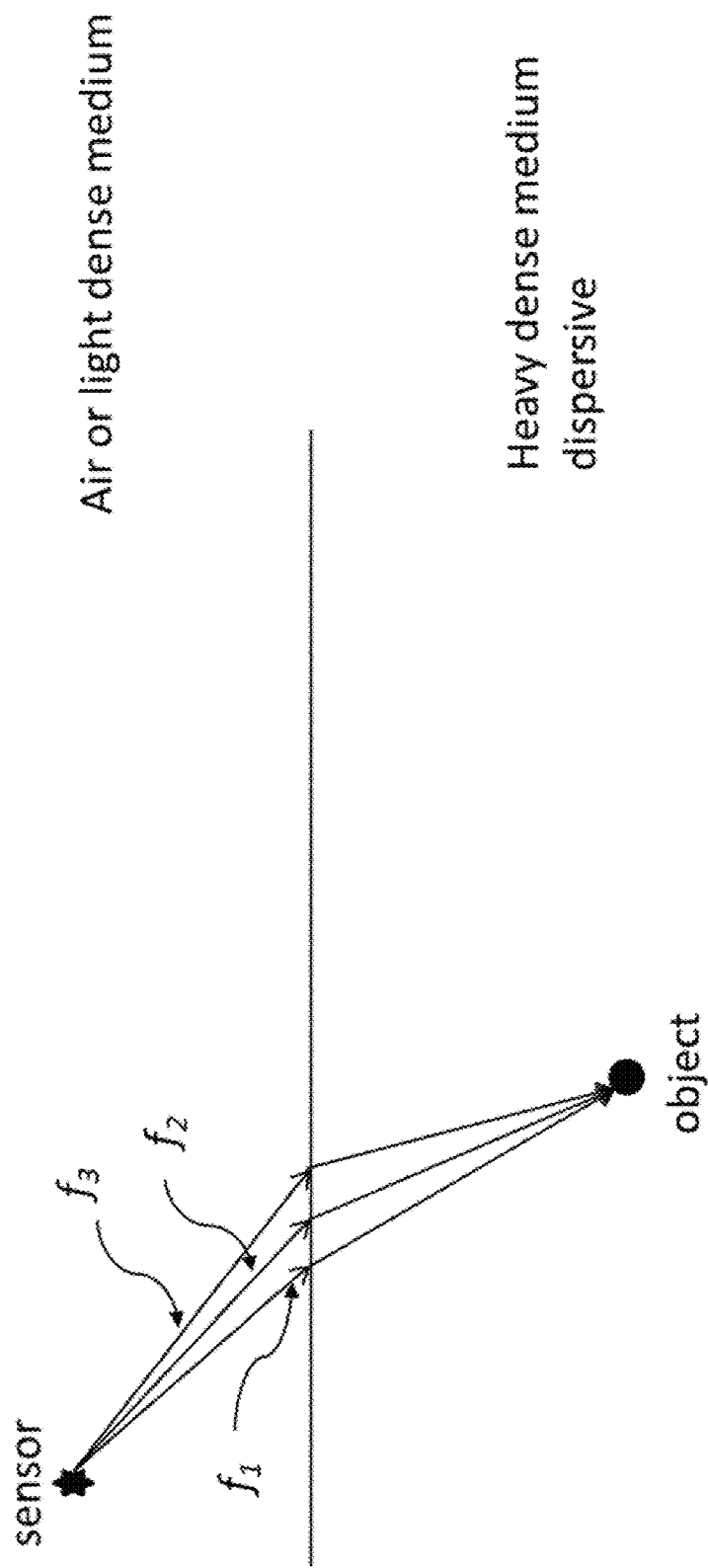
FIG. 10 shows a signal with different frequencies travels with different speeds in a dispersive medium, and will take different paths as the different frequencies propagate from the sensor to the object.

When the object is buried or existing in a dispersive medium (human body tissues, etc.), the present method is able to accurately estimate the contribution of every frequency component. It is known that wave propagation speed varies with frequency in a dispersive medium and refraction rate varies with frequency as well. FIG. 10 shows the propagation of three frequency components, where $f_1>f_2>f_3$, from a source present in air or a light dense medium to an object present in a heavy dense medium. As the refraction points on the interface are different, the three frequency components must take different paths to arrive at the object. The quality of the image using conventional time-domain UWB imaging methods depends on the time delay of the UWB signal being correctly calculated. The UWB signal containing many frequency components is assumed to travel together taking one path and propagating at one speed. The conventional method neglects the speed difference and path difference so the time delay is not accurately calculated. Therefore, the ultra-wideband characteristic of the UWB signal is not fully utilized, which causes degradation in image quality. To summarize, a UWB signal is applied in the conventional method to achieve high-resolution, but the manner in which the conventional method processes the UWB signal is more like processing a single-frequency signal. In contrast, the present method works in the frequency domain. It analyzes the refraction and propagation path for each frequency component individually and uses the associated speed to compute the phase delay. Therefore, the phase delay under each frequency in the spectrum can be accurately computed. PCM takes full advantage of the ultra-wideband characteristic of the UWB signal.

The approach that synthesizes the signals from all channels and all frequencies (Step 411) is similar to the single frequency case. The only difference is that it will have L×M×N signals to process, where L is the number of frequencies applied. The multiple frequency equation to synthesize signals is:

$$Q(\vec{r})=\sigma^2(\cos(\psi'_{mnl}))+\sigma^2(\sin(\psi'_{mnl}))$$

When the measurement is made in the frequency domain, it is assumed all frequency components have the same initial phase. Thus, the phases from all channels and all frequencies are expected to be correlated after the phase compensation step when the focal point falls in the object's location. If the measurement is taken in the time domain, the initial phases of frequency components in a UWB signal are usually unequal. Thus, an additional step that subtracts the initial phases of the frequency components in the UWB signal from the compensated phases must be taken into account in the multiple-frequency method.

After the single frequency and multiple frequency step of synthesizing the signals is complete (steps 407 and 411 respectively) then an image is constructed using the synthesized data in steps 408 or 412 respectively. The vector addition method linearly converts the output to a pixel value to form an image. The image is constructed using the previously presented equation for $P(\vec{r})$ in the variance method.

Figure 11:
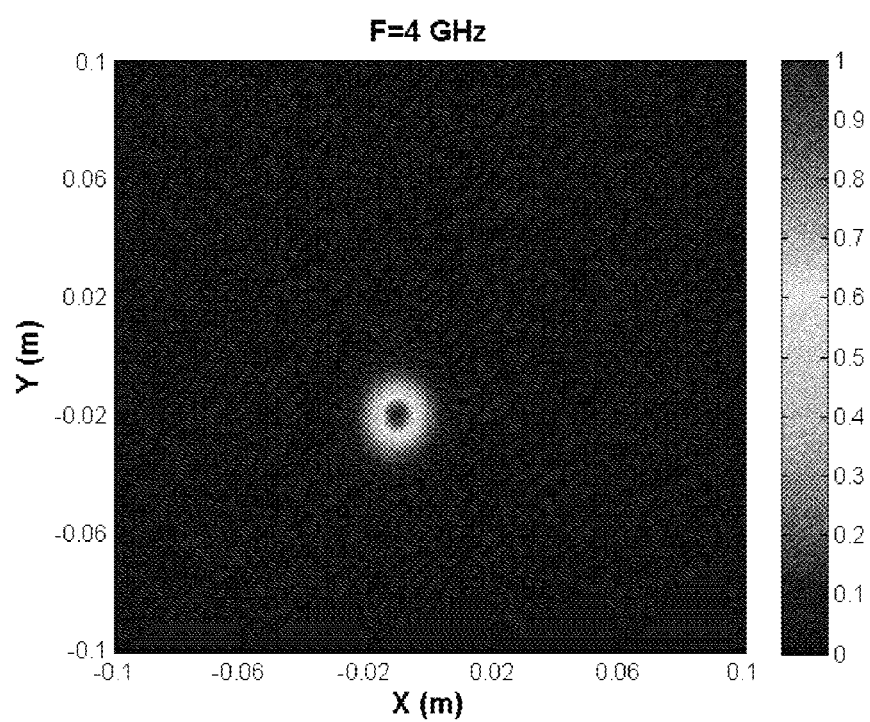
FIG. 11 shows a reconstructed image using lab measured data with the present microwave imaging method.

FIG. 11 presents a reconstructed image in the horizontal plane by the invented method with a single frequency of 4 GHz. The targeted object was a long square lumber (wood) vertically placed in the middle area of the rail system 107. The object is distinguished out from the background which is contained in a blue color and corresponds to a value of 0. FIG. 11 indicates that the present method successfully localizes the position of the object where it was placed in the experiment and shows its basic dimension in the horizontal cross plane. Microwave data required to reconstruct FIG. 11 were acquired from a fully automated microwave detection system that can be operated remotely. Such a system is described in, for example, U.S. application Ser. No. 15/094,368 entitled "Microwave Imaging Device," filed Apr. 8, 2016, which is incorporated herein by reference in its entirety for devices, methods and techniques related to microwave imaging. In the data collection process, a transmitter was arranged to stop in 24 locations (M=24) to send out a signal and a receiver stopped in 19 locations (N=19) to collect the signal. The invented method took only 1.5 seconds using a computational processor 110 to process the microwave data before FIG. 11 was obtained.

Unlike other RADAR-based algorithms using magnitudes such as the conventional Delay and Sum (DAS) that usually adds a weight term for all signals to compensate for the decay in propagation, the inventive algorithm does not require this kind of compensation. There is no need to consider the antennas' gains pattern in PCM, which is often required in methods that use magnitudes. This reduces the likeliness of causing artificial errors and also avoids any additional steps for antenna-factor calibration.

Another advantage of the present method is its efficiency. The total processing time, including phase estimation and compensation, multiple channels and multiple frequencies synthesis, and an image buildup only takes a couple of seconds on a regular personal computer. This efficiency is better than existing microwave imaging approaches. If speedup in data collection can be achieved (by means of appropriately increasing the number of antennas) and a super computer is available to run the invented method, a real-time microwave image is feasible.

The invention is not limited to the embodiments described above. Many other variations of the invention are possible and depend on the particular requirements at hand. This invention may also be used in ultra-sonic imaging and many other scenarios. Such variations and different application areas are within the scope and spirit of the invention. The invention is therefore defined with reference to the following claims.

We claim:

1. A system for producing a microwave (MW) image, the system comprising:
   a MW transmitter, configured to transmit a MW towards an object;
   a MW receiver, configured to detect a MW signal received from the object;
   a computation processor programmed to produce an image of the object using a variance of a shifted phase of a plurality of detected MW signals;
   wherein the computation processor is programmed to compute the variance of the shifted phase by
   (1) calculating a phase shift due to a wave propagation distance from the MW transmitter to the MW receiver via a focal point at a frequency of a transmitted MW,
   (2) compensating a phase of a detected MW signal using the phase shift to produce the shifted phase, and
   (3) calculating the variance of the shifted phase;
   wherein the computation processor is programmed to compute an inverse of a summation of (1) a variance of the sine of the shifted phase and (2) a variance of the cosine of the shifted phase.

2. The system of claim 1 wherein the computation processor is programmed to sum detected MW signals with phase replaced by shifted phase.

3. The system of claim 1 further comprising a controller programmed to move the MW transmitter and the MW receiver.

4. The system of claim 1 wherein the MW transmitter comprises at least one MW transmitter antenna and the MW receiver comprises at least one MW receiver antenna.

5. A method for producing a microwave (MW) image, comprising:
   transmitting a MW from a MW transmitter towards an object;
   detecting, with a MW receiver, a MW signal received from the object;
   controlling a movement of the MW transmitter and the MW receiver around the object;
   calculating wave propagation distances from the MW transmitter and the MW receiver to focal points using a frequency of a transmitted MW signal to produce a phase shift;
   compensating a phase of a detected MW signal using the phase shift to produce a shifted phase;
   calculating a variance of the shifted phase; and
   producing an image of the object using the variance of the shifted phase of a plurality of detected MW signals;
   wherein producing an image of the object further comprises computing an inverse of a summation of (1) a variance of the sine of the shifted phase and (2) a variance of the cosine of the shifted phase.

6. The method of claim 5 wherein the detected MW signal is a signal collected using a vector network analyzer represented as an S parameter.

7. The method of claim 5 wherein the detected MW signal is a time domain signal collected using an oscilloscope which has been converted to the frequency domain using a Fourier transform.

8. The method of claim 5 wherein the wave propagation distances include the distance of a path a wave propagates from the MW transmitter to a focal point and then from the focal point to the MW receiver.

9. The method of claim 5 wherein producing an image of the object further comprises treating complex-number detected MW signals as unit vectors.

10. The method of claim 9 wherein producing an image of the object further comprises calculating an average of a squared distance from unit vectors to their mean position.

11. The method of claim 5 wherein producing an image of the object further comprises summing detected MW signals with phase replaced by shifted phase.

12. A method for producing a microwave (MW) image using multiple frequencies, comprising:
   transmitting a MW from a MW transmitter towards an object;
   detecting, with a MW receiver, a MW signal received from the object;
   wherein the transmitting and detecting comprises transmitting and detecting at multiple frequencies;
   controlling a movement of the MW transmitter and the MW receiver around the object;
   calculating wave propagation distances from the MW transmitter and MW receiver to focal points using the frequencies of transmission to produce phase shifts;
   compensating a phase of detected MW signals using the phase shifts to produce shifted phases for each frequency;
   calculating a variance of the shifted phases; and
   producing an image of the object using the variance of the shifted phases of a plurality of MW signals at the multiple frequencies;
   wherein producing an image of the object further comprises computing an inverse of a summation of (1) a variance of a sine of shifted phase and (2) a variance of the cosine of the shifted phase for all frequency components.

13. The method of claim 12 wherein the MW transmitter and MW receiver comprise UWB antennas.

14. The method of claim 13 further comprising compensating the phase of detected MW signals based on a phase change in a connector on a transmitter antenna end, a phase change in a transmitter antenna, a phase change in a receiver antenna, and a phase change in a connector on a receiver antenna end.

15. The method of claim 12 wherein producing an image of the object further comprises summing multiple frequency detected MW signals with phase replaced by shifted phase.

16. The method of claim 12 wherein producing an image of the object further comprises calculating wave propagation distance taking different refractions of mediums into account.

17. A method for producing a microwave (MW) image, comprising:
    transmitting a MW from a MW transmitter towards an object;
    detecting, with a MW receiver, a MW signal received from the object;
    controlling a movement of the MW transmitter and the MW receiver around the object;
    calculating wave propagation distances from the MW transmitter and the MW receiver to focal points using a frequency of a transmitted MW signal to produce a phase shift;
    compensating a phase of a detected MW signal using the phase shift to produce a shifted phase; and
    producing an image of the object using the shifted phase of a plurality of detected MW signals,
    wherein producing an image of the object further comprises treating complex-number detected MW signals as unit vectors,
    wherein producing an image of the object further comprises calculating an average of a squared distance from unit vectors to their mean position.

18. A method for producing a microwave (MW) image using multiple frequencies, comprising:
    transmitting a MW from a MW transmitter towards an object, wherein the MW transmitter comprises an UWB antenna;
    detecting, with a MW receiver, a MW signal received from the object, wherein the MW receiver comprises an UWB antenna;
    wherein the transmitting and detecting comprises transmitting and detecting at multiple frequencies;
    controlling a movement of the MW transmitter and the MW receiver around the object;
    calculating wave propagation distances from the MW transmitter and MW receiver to focal points using the frequencies of transmission to produce phase shifts;
    compensating a phase of detected MW signals using the phase shifts to produce shifted phases for each frequency, the compensating the phase of detected MW signals including compensating the phase of detected MW signals based on a phase change in a connector on a transmitter antenna end, a phase change in a transmitter antenna, a phase change in a receiver antenna, and a phase change in a connector on a receiver antenna end; and
    producing an image of the object using the shifted phases of a plurality of MW signals at the multiple frequencies.

* * * * *